(12) United States Patent
Sha

(10) Patent No.: US 7,205,010 B2
(45) Date of Patent: Apr. 17, 2007

(54) DIETARY SUPPLEMENT COMPOSITION FOR AMELIORATING INFLAMMATORY CHANGES IN INFLUENZA PROCESS

(76) Inventor: Shinhan Sha, 2-7-11, Nishiikebukuro, Toshima-ku, Tokyo (JP)

( * ) Notice: Subject to any disclaimer, the term of this patent is extended or adjusted under 35 U.S.C. 154(b) by 281 days.

(21) Appl. No.: 10/882,202

(22) Filed: Jul. 2, 2004

(65) Prior Publication Data
US 2006/0003032 A1    Jan. 5, 2006

(51) Int. Cl.
*A61K 36/268* (2006.01)
*A61K 36/25* (2006.01)
*A61K 36/46* (2006.01)
*A61K 36/236* (2006.01)
*A61K 36/8962* (2006.01)

(52) U.S. Cl. .............. 424/756; 424/728; 424/757; 424/754; 424/769; 424/773; 424/725

(58) Field of Classification Search ............ 424/756, 424/728, 757, 754, 725, 769, 7.73
See application file for complete search history.

(56) References Cited

U.S. PATENT DOCUMENTS

2004/0161524 A1* 8/2004 Sakai et al. ............ 426/655

OTHER PUBLICATIONS

Phillipson, J. New Drugs From Nature—It Could Be Yew; Phytotherapy Research 13 (1999) pp. 2-8.*

* cited by examiner

*Primary Examiner*—Patricia Leith
(74) *Attorney, Agent, or Firm*—Finnegan, Henderson, Farabow, Garrett & Dunner, L.L.P.

(57) ABSTRACT

The invention provides a dietary supplement composition comprising ginger, *Strobilanthes cusia*, *Panax pseudo-ginseng*, *Eucommia ulmoides*, *Momordicae grosvenori*, Licorice root, and *Allium fistulosum*.

6 Claims, No Drawings

DIETARY SUPPLEMENT COMPOSITION FOR AMELIORATING INFLAMMATORY CHANGES IN INFLUENZA PROCESS

BACKGROUND OF THE INVENTION (1) Field of the Invention

The present invention relates to a dietary supplement composition for ameliorating inflammatory changes in influenza process.

(2) Description of the Related Art

Although the overall pathological mechanisms involved in the course of influenza have not been fully elucidated, the ongoing accumulation in the lung of neutrophils and macrophages could play an active role through the production of reactive oxygen species which can ultimately cause and perpetuate a tissue injury. An evidence for the presence of such an oxidative stress has suggested that antioxidants can be used as therapeutic agents.

SUMMARY OF THE INVENTION

The present inventor eagerly studied possible therapeutic agents for influenza and has found that a composition which is called MMT (a tradename, Kyotsu Kogyo Inc., Tokyo, Japan) and contains ginger, *Strobilanthes cusia, Panax pseudo-ginseng, Eucommia ulmoides, Momordicae grosvenori*, Licorice root and *Allium fistulosum*, is effective to ameliorate inflammatory changes in influenza process.

An object of the present invention is to provide a dietary supplement for ameliorating inflammatory changes in the influenza process.

The present invention is:

(1) A dietary supplement composition comprising ginger, *strobilanthes cusia, panax pseudoginseng, eucommia ulmoides, momordicae grosvenori*, licorice root, and *Allium fistulosum;*

(2) A method of ameliorating inflammatory changes in a influenza process, which comprises administrating the composition of the above item (1) to a subject.

The composition of the present invention is hereinafter referred to also as MMT.

DESCRIPTION OF THE PREFERRED EMBODIMENTS

Histologically, the main signs characterizing the influenza process are infiltration of lymphoid cells and oedema in the alveolar space, necrosis of ciliated epithelial cells and haemorrhage paralleled by the accumulation of neutrophils and macrophages, which are known to produce noxious reactive oxygen species, as appeared in the present study. Lung homogenates also showed a decrease of ascorbic acid and a raise of TNF-α which is known to be able to trigger the recruitment of leukocytes being involved in the inflammatory/thrombotic cascade with macrophage activation as observed in influenza model (Van Lenten et al., Circulation 2002; 106:1127–1132). All the above phenomena were significantly prevented either partially or totally when the herbal compound MMT was added to the diet of experimental animals. Although the precise mechanism of each single component cannot be clarified at the moment, many of its ingredients have either anti-inflammatory (Ismail et al., J Nutr Biochem. 2000; 11:536–542, Han et al., J Gerontol A Biol Sci Med Sci 2000; 55:496–503) or antioxidant properties (Hsieh et al., Life Sci., 2000; 66:1387–1400, Keum, et al., Cancer Lett. 2000; 150:41–48, Ukiya et al., J Agric Food Chem. 2002; 50:6710–5). Such overall antioxidant/anti-inflammatory properties, together with anti-asthmatic effect exerted by the alk(en)ylsulfinothioic acid alk(en)yl-esters component of *allium fistolosum* (Dorsch et al., Biochem Pharmacol 1988; 37:4479–4486) might help explaining the evident symptomatic improvement of infected mice which received MMT. The deficiency of dietary antioxidant can impair the function of lung immune system (Sabat et al., Free Radic Biol Med 2001; 30:1145–1153), and the supplementation with vitamin E has proved to improve Thl cytokine production in influenza-infected mice (Han et al., Immunology 2000; 100:487–493). Interestingly, although MMT did not alter the high virus titre in the nasal washing, it proved to significantly decrease the viral load in the lung. It can be speculated that the improved endogenous and anti-inflammatory properties exerted at a systemic and lung level plays a role in limiting viremia in the lungs.

MMT contains ginger, *Strobilanthes cusia, Panax pseudo-ginseng, Eucommia ulmoides, Momordicae grosvenori,* Licorice root, and *Allium fistulosum.*

MMT can contain these herbal ingredients in any amounts as far as the effect of the present invention is shown. However, the amounts of the herbal ingredients may vary depending on ease or pleasantness to drink, such as taste and feeling to a tongue; the type of prevailing influenza virus; the place of origin of the plants; the season of harvest of the plants; and other factors that may more or less alter the active ingredient content. The amounts thereof can be readily properly determined depending on the above factors by one of ordinary skill in the art.

MMT contains preferably 5–90%, more preferably 12–38%, most preferably 20–30% by weight of *ginger*; preferably 5–90%, more preferably 10–30%, most preferably 16–24% by weight of *Strobilanthes cusia*; preferably 5–90%, more preferably 10–30%, most preferably 16–24% by weight of *Panax pseudo-ginseng*; preferably 5–90%, more preferably 7–23%, most preferably 12–18% by weight of *Eucommia ulmoides*; preferably 1–90%, more preferably 4–14%, most preferably 7–11% by weight of *Momordicae grosvenori*; preferably 1–90%, more preferably 4–14%, most preferably 7–11% by weight of Licorice root; and preferably 0.1–30%, more preferably 1–3%, most preferably 1.6–2.4% by weight of *Allium fistulosum*, the total amount of these ingredients being 100% by weight. Usually, MMT contains 25% by weight of *ginger,* 20% by weight of *Strobilanthes cusia,* 20% by weight of *Panax pseudo-ginseng,* 15% by weight of *Eucommia ulmoides,* 9% by weight of *Momordicae grosvenori,* 9% by weight of Licorice root, and 2% by weight of *Allium fistulosum.*

MMT may be provided in an amount of 3 g per a bag and can be received in a dose of about 0.1 to about 20 g, preferably 3 to 9 g per a day per an adult, with cold or hot water. MMT can be easily dissolved in water. No detrimental side effect of MMT has not been found.

*Ginger* is the rhizome (rhizoma), root stock(s) or the like of a ginger, *Zingiber officinale* Roscoe, belonging to the family Zingiberaceae. It is also known as a commercially available herbal medicine, which is effective as a stomachic or antitussive, or to warm the body.

*Strobilanthes cusia* is a plant species belonging to the family Acanthaceae. A herbal medicine derived from the plant is commercially available and known to be effective for cold and to loosen phlegm.

*Panax pseudo-ginseng* is a plant species belonging to the family Araliaceae and its root is commercially available as a herbal medicine called "Denhichi". This herbal medicine has been known to improve lipid metabolic failure and control hypertension and pain relief. *Panax pseudo-ginseng* and "Denhichi" are exchangeably used in the present invention.

*Eucommiae ulmoides* is a plant species which grows wild in China. It's young leaves, dried bark, stems and/or nuts (fruit) are a commercially available as a herbal medicine generally known as *Eucommia bark,* Chinese gutta percha or "Tochu". *Eucommiae ulmoides, Eucommia bark,* Chinese gutta percha and "Tochu" are exchangeably used in the present invention. This herbal medicine has been known to reduce hypertension and high blood lipid level.

*Momordicae grosvenori* is a plant species belonging to the family Cucurbitaceae and its fruit is commercially available as a herbal medicine also called *momordicae fructus* or "Rakanka". *Momordicae grosvenori, momordicae fructus* and "Rakanka" are exchangeably used in the present invention. This herbal medicine has been known as a low-calorie sweetener and also to be effective to reduce the inflammation of a throat due to cold, loosen phlegm or relieve coughing.

Licorice root is obtained from the roots or kernels of *Glycyrrhiza glabra* Linn or the like and also called "*glycyrrhiza*", "licorice", "liquorice", "*glycyrrhiza radix*", or "Kanzo". These terms are exchangeably used in the present invention. This herbal medicine has been known to alleviate convulsions and pain and have a detoxification effect.

*Allium fistulosum* is a plant species belonging to the family Liliaceae and also known to be effective for cold, headache and external wound.

The present composition can be prepared for example by the following procedures, which do not however restrict the preparation method of the present composition by any means.

Each of ginger, *Strobilanthes cusia, Panax pseudo-ginseng, Eucommia ulmoides, Momordicae grosvenori,* Licorice root, and *Allium fistulosum* is minced and extracted with hot water at 60° C.–100° C. for 0.5–2 hr or with ethanol or a mixed solution of ethanol and water in a ratio of 100:0–0:100 at room temperature to 100° C. (extraction step). The extract may be subjected to filtration and concentration steps, as need arises. By processing the extract under hot air, the powder or granule of each herbal ingredient is obtained and mixed with one another in an appropriate amount to prepare a composition of the present invention.

Based on the following experiments, it is suggested that the present composition, MMT, has the potential to be applied in clinical practice.

Summary of Experiments

Healthy mice were allocated into three groups: A) control; B) influenza virus-infected group (Group I) and C) dietary supplement (MMT)-treated and influenza-infected group (Group I-MMT). Mice were infected intranasally with 30 µl of 75HA units of the virus. Group I-MMT received 5 mg of MMT t.i.d. Signs of infection, total inflammatory cell counts in nasal washings, virus titres in lungs homogenates and plasma malonyldialdehyde (MDA) were serially examined for 8 days. Bronchoalveolar lavage fluid (BALF) and lung tissue collected from the sacrificed mice were examined for superoxide radical production and for MDA, ascorbic acid and TNFα activities. MMT markedly blunted the nasal signs of virus infection and reduced the febrile response. Formazan-positive cells, MDA in the lung extract and the plasma, and TNFα in the lung tissue significantly increased during viral infection, but a significant improvement was observed in Group I-MMT. SOD, catalase activities and ascorbic acid significantly decreased in the infected groups (Group I), but not in Group I-MMT. The MMT-treated group also showed a significant decrease of viral titre in the lung. No toxicity was detected up to dosages over 50-fold higher. It is suggested that MMT, a safe natural composition, has a potential to be provided as a dietary supplement and applied in clinical practice.

Experimental Design

Healthy adult Swiss albino mice were maintained in a pathogen-free environment. After acclimation for four days, the animals were allocated into three groups each of 84 animals: A) healthy control; B) influenza-infected group (Group I) and C) MMT-treated and influenza-infected group (Group I-MMT). Under mild ether anaesthesia, mice were infected intranasally with 30 µl of 75HA units of influenza virus, type A/Hong Kong/8/68 virus. The control group were given same quantity of sterile allantoic fluid. Group I-MMT orally received 15 mg of a dietary supplement divided in three doses daily till the day they were sacrificed. MMT contained ginger, *Strobilanthes cusia, Panax pseudo-ginseng, Eucommia ulmoides, Momordicae grosvenori,* Licorice root, and *Allium fistulosum.*

Clinical signs of infection were observed throughout the study period, while the total count of inflammatory cells in nasal washings and the virus titres of lungs homogenates were determined throughout 8 days (Toms et al., Br. J. Exp. Pathol. 1977; 58:444–458).

Biochemical Measurement of Plasma

Antioxidant Status

Blood samples were collected from the sacrificed animals on the day of sacrifice and immediately refrigerated in ice. The plasma was separated by centrifugation at 4° C. Plasma malonyldialdehyde (MDA) was assayed by the Yagi's method modified by adding 0.01% butylated-hydroxytoluene. Tetraethoxypropane served as a standard source of malonyldialdehyde (MDA) which is one of thiobarbituric reactant substances (TBARs). All samples were processed in duplicate.

Bronchoalveolar Lavage Fluid (BALF) Collection and Lung Tissue Storage

On the forth day, when the maximum pathological effects were usually expected, half number of each group of mice were anesthetized with 5% halothane and a BAL was performed to obtain a cell pellet. The mice were then sacrificed by cervical dislocation, the lungs were exposed and perfused with 5 ml of cold phosphate buffer saline (PBS), pH 7.2 through the right ventricle.

Assessment of Superoxide Radical Production

Cell suspension was mixed with 0.2% Nitroblue-tetrazolium (NBT) in PBS and slides were counterstained with Leishman's stain. Formazan positive cells (F+) were blindly scored. Results were all expressed as the number of F+ cells per 200 cells.

Cellular and Biochemical Determination

Lungs were homogenized and assayed for ascorbic acid concentrations by HPLC with electro-chemistry. TNFα activity from tissue culture supernatants was assessed by quantitating a cytolytic activity against the L929 target cell line in the presence of *actinomycin D*. MDA were assessed as described above.

Toxicological Studies

Separate groups of mice received a dose of MMT (5, 15, or 30 g/kg of body weight per day) or sterile water via oral gavage (10 ml/kg of body weight) once a day for 14 consecutive days. Twenty-four hours after the administration of the last dose, blood was withdrawn for biochemical studies and the animals were sacrificed to evaluate signs of toxicity in several tissues.

Statistical Analysis

Results were expressed as mean±standard error (S.E.). Statistical comparison among the groups was done by "paired t test" with p values less than 0.05 accepted as being statistically significant. Correlations were tested using the Kendall-Tau test for non-parametric data.

Results

Infected mice developed a disease with signs such as fever, enhanced nasal discomfort and general lethargy. The febrile response caused by the virus used in these experiments began about 12 h after infection and lasted approximately 48 h. Oral administration of MMT markedly blunted the nasal signs of virus infection in this model and the decrease in motor activity. As compared to Group I, concomitant administration of 15 mg of MMT caused a 46% reduction in the area-under-the-curve measurement for the increase in body temperature ($p<0.05$, data not shown). Formazan-positive cells increased by 80% during viral infection but lowered to 44% after supplementation. Superoxide dismutase and catalase activities significantly decreased in the infected group (Group I). MMT-treated group (Group I-MMT) showed values comparable to the control group (Table 1).

TABLE 1

SOD and catalase activity in BAL pellets
Effect of influenza and MMT supplementation (mean ± SD)

| Group | SOD (U/mg protein) | Catalase (U/mg protein) |
| --- | --- | --- |
| Healthy control | 14.2 ± 1.1 | 29.7 + 1.9 |
| Influenza model untreated | 9.8 + 1.2* | 23.7 ± 2.3* |
| Influenza model MMT-treated | 12.9 ± 0.8§ | 28.1 ± 2.5§ |

*$p < 0.05$ vs healthy control
§$p < 0.05$ vs untreated group

The supplementation with MMT enabled a significant reduction of the content of MDA in the lung extract and the plasma as well as of TNF-α in the lung tissue, and a restoration of ascorbic acid ($p<0.05$ vs Group I, Table 2).

TABLE 2

MDA, TNF-α and ascorbic acid in whole
lung homogenates and plasma MDA
Effect of influenza and MMT supplementation (mean ± SD)

| Group | Plasma MDA (μmol/L) | Lung MDA (nmol/mg protein) | Lung TNF-α (ng/g tissue) | Ascorbic Acid (μg/g lung tissue) |
| --- | --- | --- | --- | --- |
| Healthy control | 0.29 ± 0.11 | 0.49 ± 0.07 | 2.1 ± 0.6 | 79.7 ± 7.9 |
| Influenza model-untreated | 0.61 ± 017* | 0.98 ± 0.15* | 15.6 ± 3.7* | 52.2 ± 8.2* |
| Influenza model-MMT-treated | 0.33 ± 0.12§ | 0.55 ± 0.06§ | 7.8 ± 3.1§ | 73.8 ± 4.6§ |

*$p < 0.05$ vs healthy control
§$p < 0.05$ vs untreated group

Virus titre in the nasal washing significantly increased 36 h after the virus inoculation and reached a maximum of 50% tissue culture infective doses ($TCID_{50}$) on the third day ($3.88\pm0.33$ $\log_{10}$ $TCID_{50}^S$/ml). MMT-treated animals did not show any significant difference but the total count of inflammatory cells in the nasal washing showed an early significant decrease which was maintained throughout the study period ($p<0.05$). Furthermore, although viral activity in the lung homogenate was not as high as in the nasal washing, it significantly decreased in MMT-supplemented animals ($p<0.05$ vs untreated group).

MMT Toxicology Tests

MMT was not associated with any drug-related toxicity even at dosages as high as 30 g/kg/day for 14 consecutive days, which were over 50-fold higher than the dosages required to protect mice against the effects of influenza virus infection.

The invention claimed is:

1. A dietary supplement composition comprising a water extract, alcohol extract, or water and alcohol extract of ginger; a water extract, alcohol extract, or water and alcohol extract of *Strobilanthes cusia;* a water extract, alcohol extract, or water and alcohol extract of *Panax pseudo-ginseng;* a water extract, alcohol extract, or water and alcohol extract of *Eucommia ulmoides;* a water extract, alcohol extract, or water and alcohol extract of *Momordicae grosvenori;* a water extract, alcohol extract, or water and alcohol extract of Licorice root; and a water extract, alcohol extract, or water and alcohol extract of *Allium fistulosum.*

2. The composition according to claim 1, which contains 5–90% by weight of a water extract, alcohol extract, or water and alcohol extract of ginger; 5–90% by weight of a water extract, alcohol extract, or water and alcohol extract of *Strobilanthes cusia;* 5–90% by weight of a water extract, alcohol extract, or water and alcohol extract of *Panax pseudo-ginseng;* 5–90% by weight of a water extract, alcohol extract, or water and alcohol extract of *Eucommia ulmoides;* 1–90% by weight of a water extract, alcohol extract, or water and alcohol extract of *Momordicae grosvenori;* 1–90% by weight of a water extract, alcohol extract, or water and alcohol extract of Licorice root; and 0.1–30% by weight of a water extract, alcohol extract, or water and alcohol extract of *Allium fistulosum,* the total amount of these ingredients being 100% by weight.

3. The composition according to claim 2, which contains 12–38% by weight of a water extract, alcohol extract, or water and alcohol extract of ginger; 10–30% by weight of a water extract, alcohol extract, or water and alcohol extract of *Strobilanthes cusia;* 10–30% by weight of a water extract, alcohol extract, or water and alcohol extract of *Panax pseudo-ginseng;* 7–23% by weight of a water extract, alcohol extract, or water and alcohol extract of *Eucommia ulmoides;* 4–14% by weight of a water extract, alcohol extract, or water and alcohol extract of *Momordicae grosvenori;* 4–14% by weight of a water extract, alcohol extract, or water and alcohol extract of Licorice root; and 1–3% by weight of a water extract, alcohol extract, or water and alcohol extract of *Allium fistulosum,* the total amount of these ingredients being 100% by weight.

4. The composition according to claim 3, which contains 20–30% by weight of a water extract, alcohol extract, or water and alcohol extract of ginger; 16–24% by weight of a water extract, alcohol extract, or water and alcohol extract of *Strobilanthes cusia;* 16–24% by weight of a water extract, alcohol extract, or water and alcohol extract of *Panax pseudo-ginseng;* 12–18% by weight of a water extract, alcohol extract, or water and alcohol extract of *Eucommia ulmoides*; 7–11% by weight of a water extract, alcohol extract, or water and alcohol extract of *Momordicae grosvenori*; 7–11% by weight of a water extract, alcohol extract, or water and alcohol extract of Licorice root; and 1.6–2.4% by weight of a water extract, alcohol extract, or water and alcohol extract of *Allium fistulosum*, the total amount of these ingredients being 100% by weight.

5. The composition according to claim 4, which contains 25% by weight of a water extract, alcohol extract, or water and alcohol extract of ginger; 20% by weight of a water extract, alcohol extract, or water and alcohol extract of *Strobilanthes cusia*; 20% by weight of a water extract, alcohol extract, or water and alcohol extract of *Panax pseudo-ginseng*; 15% by weight of a water extract, alcohol extract, or water and alcohol extract of *Eucommia ulmoides*; 9% by weight of a water extract, alcohol extract, or water and alcohol extract of *Momordicae grosvenori*; 9% by weight of a water extract, alcohol extract, or water and alcohol extract of Licorice root; and 2% by weight of a water extract, alcohol extract, or water and alcohol extract of *Allium fistulosum*.

6. A method of ameliorating inflammatory changes in an influenza process, which comprises administering the composition of any one of claims 1 to 5 to a subject.

* * * * *